United States Patent [19]

Shinno et al.

[11] Patent Number: 4,776,849
[45] Date of Patent: Oct. 11, 1988

[54] MEDICAL INSTRUMENT

[75] Inventors: Kouji Shinno, Yamanashi; Hitoshi Kuboki, Kofu, both of Japan

[73] Assignee: Terumo Kabushiki Kaisha, Tokyo, Japan

[21] Appl. No.: 37,514

[22] Filed: Apr. 13, 1987

Related U.S. Application Data

[63] Continuation of Ser. No. 792,834, Oct. 30, 1985, abandoned.

[30] Foreign Application Priority Data

Nov. 6, 1984 [JP] Japan .................. 59-233768

[51] Int. Cl.$^4$ ............................................. A61M 25/00
[52] U.S. Cl. .................................... 604/283; 604/905
[58] Field of Search .............. 604/29, 283, 303 R, 604/410, 411, 414, 415, 905; 156/272.2, 272.4, 272.6, 275.5

[56] References Cited

U.S. PATENT DOCUMENTS 4,439,188  3/1984  Demehey et al. .................. 604/29

FOREIGN PATENT DOCUMENTS 2913676  10/1980  Fed. Rep. of Germany ... 156/272.6
3238299  12/1983  Fed. Rep. of Germany ... 128/303 R

*Primary Examiner*—C. Fred Rosenbaum
*Assistant Examiner*—Frank Wilkens
*Attorney, Agent, or Firm*—Burns, Doane, Swecker & Mathis

[57] ABSTRACT

A medical instrument is assembled by inserting a mating portion of a first tubular member of flexible resin having a Shore D hardness of 45 or lower into a mating portion of a second tubular member of flexible resin having a Shore D hardness of 45 or lower. The mating portions are joined with a curable, preferaly UV curable, adhesive which shows a Shore D hardness of 70 or lower after curing, thereby forming a firm bond.

3 Claims, 1 Drawing Sheet

MEDICAL INSTRUMENT

This application is a continuation, of application Ser. No. 792,834, filed Oct. 30, 1985 now aband.

BACKGROUND OF THE INVENTION

This invention relates to a medical instrument comprising mutually bonded tubular members of flexible resin.

In general, most medical instruments include a plurality of parts of soft or flexible material which are bonded to one another. One such example is a winged venous infusion needle assembly. A needle is secured in a hub or connector of flexible polyvinyl chloride resin which is, in turn, bonded or connected to a tube of flexible polyvinyl chloride resin with an adhesive of the solvent type using, for example, tetrahydrofuran (THF) and methyl ethyl ketone (MEK). The use of solvent-type adhesive, however, gives rise to a number of problems. (1) Solvent attacks parts to be bonded which become brittle or weak and will eventually be broken. (2) Some material is dissolved from parts by solvent and will undesirably block a flowpath. (3) Residual solvent leaves the risk of toxicity. Medical instruments having parts bonded with such solvent-type adhesive suffer from these and other problems. There is the need for a technique capable of bonding parts without using an organic solvent.

SUMMARY OF THE INVENTION

It is, therefore, an object of the present invention to provide a novel and improved medical instrument comprising flexible material parts bonded with an increased bond strength without using a conventional organic solvent-containing adhesive.

According to the present invention which attains the above object, there is provided a medical instrument comprising:

a first tubular member of a flexible resin having a Shore D hardness of not higher than 45, and a second tubular member of a flexible resin having a Shore D hardness of not higher than 45, mated over the first tubular member, characterized in that the mating portions of the first and second tubular members are bonded with a curable adhesive which shows a Shore D hardness of not higher than 70 after curing.

The shore D hardness used herein is as defined by ASTM D 2240.

In one preferred embodiment, the first tubular member includes a male mating wall provided with at least circumferential groove where the curable adhesive is accommodated. Correspondingly, the second tubular member includes a female mating wall. The male wall of the first tubular member is inserted or engaged in the female wall of the second member.

Preferably, the curable adhesive is of the ultraviolet radiation curable type.

BRIEF DESCRIPTION OF THE DRAWINGS

The above and other objects, features, and advantages of the present invention will be better understood by reading the following description taken in conjunction with the accompanying drawings, in which.

DETAILED DESCRIPTION OF THE PREFERRED EMBODIMENTS

The present invention provides a medical instrument comprising at least two flexible tubular members engaged with one another. The engagement between the members is bonded with a curable adhesive exhibiting a hardness compatible with the hardness of the members. In the present disclosure, that tubular member which comes inside the engagement is referred to as a first tubular member and that tubular member which comes outside the engagement is referred to as a second tubular member.

The medical instruments to which the present invention is applicable are blood and fluid transfusion sets, dialysis circuits, and winged venous infusion needle assemblies, but not limited thereto as long as they have at least one engagement between members.

The medical instrument of the present invention is described with reference to the drawings. Although the bonding of a hub or connector with a tube as used in a winged infusion needle assembly is described as preferred embodiments of the present invention, it should, of course, be understood that that present invention is not limited to these illustrated embodiments. The basic concept of the present invention is to use a curable adhesive instead of a conventional, commonly used solvent-type adhesive. The term curable adhesive used herein means that the adhesive will cure after the lapse of a predetermined time from its application to any member. Some illustrative, nonlimiting examples of the curable adhesives include ultraviolet (UV) curable adhesives, cyanoacrylate instant adhesives, epoxy resin base adhesives, hot melt adhesives, and acrylic adhesives.

Figure 1:
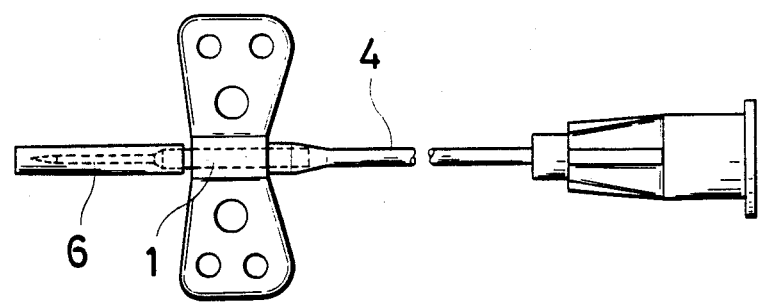
FIG. 1 is a plan view of a typical winged infusion needle assembly to which the present invention is applied.

FIG. 1 shows an overall winged venous infusion needle assembly as a typical example of the medical instrument to which the present invention is applicable. The present invention is not limited to the winged infusion needle assembly, but is applicable to any medical instrument.

Figure 2:
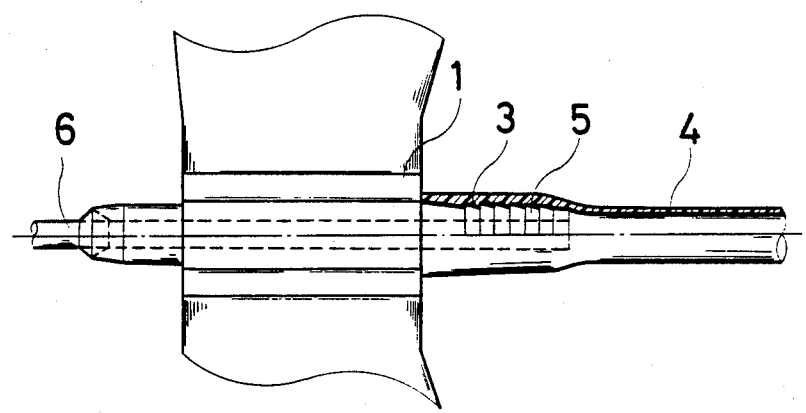
FIGS. 2 and 3 are partially cross sectional elevations of different embodiments of the medical instrument of the present invention, particularly illustrating the engagement between two parts.

FIG. 2 is an enlarged view of a wing-supporting hub portion of the assembly. More specifically, the embodiment shown in FIG. 2 illustrates the engagement or bonding of a winged hub 1 and a tube 4 of the winged infusion needle assembly. In this embodiment, the hub 1 is the first tubular member and the tube 4 is the second tubular member. The hub 1 has a pair of oppositely extending wings (partially shown) and a bore in which the base of a needle 6 is fixedly secured. The hub 1 includes a tubular male portion extending opposite to the needle 6. The male portion is preferably formed with at least one, preferably a plurality of circumferential or spiral grooves or ribs 5. One end of the tube 4 constitutes a female portion into which the hub male portion is inserted and engaged.

Figure 3:
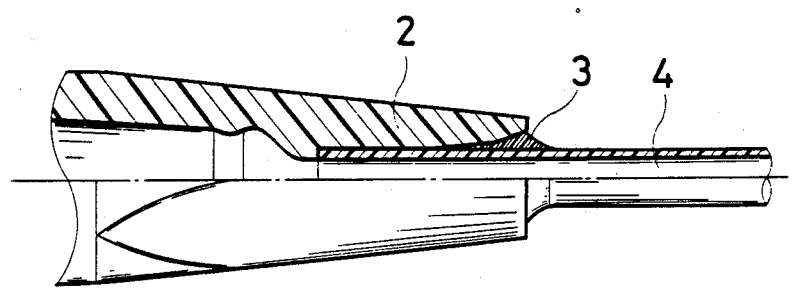

FIG. 3 illustrates another embodiment of the winged infusion needle assembly. More specifically, this embodiment illustrates the engagement or bonding of a connector 2 and a tube 4 of the winged infusion needle assembly. In this embodiment, the tube 4 is the first tubular member and the connector 2 is the second tubular member. One end of the tube 4 constitutes a male portion while one end of the connector 2 constitutes a female portion. The tube male portion is inserted in and engaged with the connector female portion.

In these embodiments, each of hub 1, connector 2, and tube 4 is formed of a flexible resin material having a Shore D hardness of 45 or lower. Resin materials having a Shore D hardness of higher than 45 fail to achieve an critical improvement in bond strength irrespective of a proper choice of the hardness of adhesive as will be described hereinafter. Examples of the resin materials have a Shore D hardness of 45 or higher include flexible polyvinyl chloride (PVC), vinyl chloride elastomers, and styrene elastomers. The hub or connector and the tube to be joined may be formed of the same or different materials as will become apparent from the experimental data.

The hub 1 or connector 2 and the tube 4 both of materials having such a specific hardness are bonded with a curable adhesive 3. Particularly, the mating male and female portions are bonded with the adhesive.

The curable adhesives used herein should show a Shore D hardness of 70 or lower after they have been cured. The use of such adhesives produces at least 20% increase in bond strength as compared with the use of adhesives which provide a Shore D hardness of higher than 70 after curing. No significant bond strength is achievable when the members to be joined and/or the cured adhesive does not meet the above-defined hardness requirements.

Most preferred, but nonlimiting examples of the curable adhesives used herein are UV curable adhesives including polyester acrylate, epoxy acrylate, and polyurethane acrylate types. The term UV curable adhesive used herein means that it cures or hardens upon exposure to electromagnetic radiation of ultrashort wave such as ultraviolet rays and γ-rays.

Referring to FIG. 2 again, the mating portion of the hub 1 or first tubular member in one preferred embodiment is formed with several circumferential grooves or ribs 5 where the curable adhesive 3 accommodates. The instrument may be assembled by applying the adhesive to the ribbed surface of the hub mating portion and then inserting the adhesive-coated portion of the hub into the mating portion of the tube 4 or the second tubular member. It is desirable for the mating portion of the hub 1 to have an outer diameter slightly larger than the inner diameter of the tube 4. After insertion, the hub-tube engagement is exposed for curing to any desired curing factor such as UV radiation, γ-rays, and heat depending on the particular type of adhesive used. It will be understood that the grooves or ribs 5 in the male mating portion of the hub 1 also serve to mechanically engage and retain the tube 4.

In the embodiment shown in FIG. 3, in order to provide a configuration capable of accommodating the adhesive, the mating portion of the connector 2 or second tubular member is formed to have an outward flaring inner surface geometry or an inner diameter slightly larger than the outer diameter of the tube 4 or first tubular member. After the tube 4 is inserted into the connector 2, an outwardly flaring space defined between their mating portions is filled with a curable adhesive. The tube-connector engagement is exposed for curing to any desired curing factor such as UV radiation, γ-rays, and heat depending on the particular type of adhesive used.

Since the assemblies or instruments prepared according to the present invention are intended for medical use, they are finally sterilized, for example, by ethylene oxide gas, autoclave, or γ-ray sterilization. When the adhesive used is of UV curable type, γ-ray exposure is effective to carry out curing and sterilization at the same time.

In order to determine the effectiveness of the present invention, we carried out a number of experiments. Some are given below.

EXPERIMENT

The assemblies of hub 1-tube 4 and connector 2-tube 4 as shown in FIGS. 2 and 3 were prepared. The materials used for the respective parts are shown below. (phr: part per hundred parts of resin)

| Resin No. | Material | Shore D hardness |
|---|---|---|
| 1 | Polyvinyl chloride resin + 65 phr plasticizer | 25 |
| 2 | Polyvinyl chloride resin + 55 phr plasticizer | 35 |
| 3 | Polyvinyl chloride resin + 40 phr plasticizer | 38 |

The adhesive used is a group of UV curable polyurethane acrylate adhesives commercially available from Toa Synthetic Chemicals K.K.

| Adhesive No. (Grade No.) | Shore D hardness after curing |
|---|---|
| 1 (3576K4) | 60 |
| 2 (3596) | 64 |
| 3 (3564K1) | 66 |
| 4 (3564K4) | 70 |
| 5 (3603) | 73 |
| 6 (3583) | 84 |

Using these materials, a set of 5 specimens was prepared for each of assemblies having different material combinations. The specimens were determined for bond strength using an Autograph DCS-100 tensile tester manufactured by Shimazu Mfg. K.K. operating at a pulling speed of 50 mm/min. Five measurements were averaged for each set.

The results are shown in Table 1.

TABLE 1

| Resin No. (Shore D hardness) | | Adhesive No. (Shore D hardness*) | Bond strength kg |
|---|---|---|---|
| Hub | Tube | | |
| 1(25) | 1(25) | 1(60) | 2.8 |
| 1(25) | 1(25) | 2(64) | 2.8 |
| 1(25) | 1(25) | 3(66) | 2.7 |
| 1(25) | 1(25) | 4(70) | 2.5 |
| 1(25) | 1(25) | 5(73) | 2.1 |
| 1(25) | 1(25) | 6(84) | 2.0 |
| 3(38) | 2(35) | 1(60) | 2.8 |
| 3(38) | 2(35) | 2(64) | 2.7 |
| 3(38) | 2(35) | 3(66) | 2.7 |
| 3(38) | 2(35) | 4(70) | 2.7 |
| 3(38) | 2(35) | 5(73) | 2.2 |
| 3(38) | 2(35) | 6(84) | 2.0 |
| Connector | Tube | | |
| 3(38) | 1(25) | 1(60) | 2.8 |
| 3(38) | 1(25) | 2(64) | 2.8 |
| 3(38) | 1(25) | 3(66) | 2.7 |
| 3(38) | 1(25) | 4(70) | 2.6 |
| 3(38) | 1(25) | 5(73) | 2.1 |
| 3(38) | 1(25) | 6(84) | 2.1 |

*Shore D hardness of cured adhesive is given in parenthesis.

EFFECT OF THE INVENTION

The medical instrument of the present invention has the following benefits.

(1) Since a conventional solvent-type adhesive is not used to bond parts with each other, all of the problems resulting from the solvent are eliminated, for example, deterioration of part material by solvent, blockage of a flowpath by dissolved material, and toxicity of residual solvent.

(2) The cured hardness of the curable adhesive is chosen so as to be compatible with the hardness of first and second tubular members to be joined, insuring a firm bond. A choice of those adhesives having a cured hardness of 70 or lower in Shore D hardness increases the bond strength by at least 20% as seen from Table 1.

(3) The use of a curable adhesive of ultraviolet curable type provides an additional benefit that instrument sterilization and adhesive curing can be effected at the same time by exposure to gamma radiation.

(4) The provision of circumferential grooves on the male portion of the first tubular member ensures an enhanced bond strength.

What we claim is:

1. A tubular member containing medical instrument having at least one engagement between tubular members comprising
   a first tubular member of a flexible resin having a Shore D hardness of not higher than 45, and
   a second tubular member of a flexible resin having a Shore D hardness of not higher than 45, mated over said first tubular member, wherein
   the mated portions of said first and second tubular members are bonded with a curable organic-solvent free adhesive which shows a Shore D hardness of not higher than 70 after curing.

2. A medical instrument according to claim 1 wherein said first tubular member includes a male mating wall provided with at least one circumferential groove where said curable adhesive is accommodated.

3. A medical instrument according to claim 1 wherein said curable adhesive is of the ultraviolet radiation curable type.

* * * * *

UNITED STATES PATENT AND TRADEMARK OFFICE
CERTIFICATE OF CORRECTION

PATENT NO. : 4,776,849

DATED : October 11, 1988

INVENTOR(S) : KOUJI SHINNO et al

It is certified that error appears in the above-identified patent and that said Letters Patent is hereby corrected as shown below:

On page 1, in the Abstract, line 6, amend "preferaly" to -- preferably --.

In column 1, line 27, amend "the" to -- thus a --.

Signed and Sealed this

Twenty-first Day of November, 1989

Attest:

JEFFREY M. SAMUELS

Attesting Officer     Acting Commissioner of Patents and Trademarks